(12) United States Patent
Sloley et al.

(10) Patent No.: US 6,593,340 B1
(45) Date of Patent: Jul. 15, 2003

(54) PHARMACEUTICAL COMPOSITIONS CONTAINING N-PROPARGYLPHENTERMINE AND RELATED ANALOGS TO TREAT NEURODEGENERATION AND/OR DEPRESSION

(75) Inventors: Brian D. Sloley, Edmonton (CA); Liana Urichuk, Beaumont (CA); Lei Ling, Edmonton (CA); Glen Baker, Edmonton (CA); Ronald Coutts, Edmonton (CA); Jacqueline Shan, Edmonton (CA)

(73) Assignee: CV Technologies, Inc., Edmonton (CA)

( * ) Notice: Subject to any disclaimer, the term of this patent is extended or adjusted under 35 U.S.C. 154(b) by 0 days.

(21) Appl. No.: 09/794,058

(22) Filed: Feb. 28, 2001

Related U.S. Application Data

(60) Provisional application No. 60/185,363, filed on Feb. 28, 2000.

(51) Int. Cl.$^7$ ........................ C07D 213/02; A61K 31/44
(52) U.S. Cl. ........................ 514/307; 514/311; 514/357; 514/646; 546/139; 546/152; 546/329; 564/305
(58) Field of Search ................................. 546/139, 152; 514/307, 311, 357, 646; 564/305

(56) References Cited

U.S. PATENT DOCUMENTS 3,067,101 A * 12/1962 Easton et al. ................ 514/671

* cited by examiner

Primary Examiner—Zinna Northington Davis
(74) Attorney, Agent, or Firm—Rothwell, Figg, Ernst & Manbeck

(57) ABSTRACT

The present invention relates to N-propargylphentermine and its derivatives and the neuroprotective and antidepressant activity of such compounds as well as therapeutic methods for such compounds.

16 Claims, No Drawings

PHARMACEUTICAL COMPOSITIONS CONTAINING N-PROPARGYLPHENTERMINE AND RELATED ANALOGS TO TREAT NEURODEGENERATION AND/OR DEPRESSION

This nonprovision application claims the benefit of U.S. Provisional Application No. 60/185,363, filed Feb. 28, 2000.

FIELD OF THE INVENTION

This present invention relates to N-propargylphentermine and certain of its substituted analogues and their salts. The present invention relates to such compounds as they have neuroprotectant and/or antidepressant activities. The present invention also relates to pharmaceutical compositions including such compounds as an active ingredient. The present invention further relates to the therapeutic use of such compounds.

BACKGROUND OF THE INVENTION

No references have been noted in the prior art regarding N-propargylphentermine and its use as a neuroprotective compound.

While references to N-propargyl-N-methylalkylamines as selective monoamine exidase-B inhibiting and neuroprotective compounds are noted, such compounds are tertiary amines. Birkmayer et al., Journal of Neurotransmission 64:113–127 (1985); Yu et al., Journal of Medicinal Chemistry 35:3705–3713 (1992); Yu et al., Journal of Neurochemistry 63:1820–1828(1994). The present invention is primarily related to secondary amines.

SUMMARY OF THE INVENTION

It has now been discovered that N-propargylphentermine-related compounds having the following general formula:

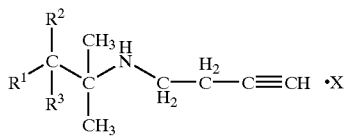

where

R$^1$ and/or R$^2$ and/or R$^3$=one or more phenyl, pyridinyl, pyrryl, furanyl, quinoline, isoquinoline, indolyl, naphthyl, thienyl or similar arylalkyl (where arylalkyl is defined as an aromatic structure such as a phenyl, pyridinyl, pyrryl, furanyl, quinoline, isoquinoline, indolyl, naphthyl, thienyl or similar aryl group combined with a linear or branched or cyclic alkyl chain consisting of between 1 and 10 carbons), substituted arylakyl, (where substituted arylalkyl is defined as an aromatic structure such as a phenyl, pyridinyl, pyrryl, furanyl, quinoline, isoquinoline, indolyl, naphthyl, thienyl or similar aryl group combined with a linear or branched or cyclic alkyl chain consisting of between 1 and 10 carbons and substituted with one or more groups consisting of Cl, F, Br, OH, CF$_3$, NH$_3$, NO$_2$, alkoxy, alkythiol, thiol or similar substitution), CH$_3$, Cl, F, Br, OH, CF$_3$ NH$_3$ NO$_2$, alkoxy, alkylthiol, thiol or similar C$_1$–C$_8$ alkyl, substituted alkyl, alkenyl, alkynyl groups,.

X when present is a salt-forming acid; have useful therapeutic activity as neuroprotective, antidepressant and/or anorexia agents.

The present invention includes methods of protecting the nervous system, treating neurodegenerative diseases or depression, suppressing appetite or controlling weight gain by administering, enterally or parenterally or as an injection, the compounds of the present invention in an animal or human at a dose of 0.01 mg/kg per day to 100 mg/kg per day. The compounds are usually but not necessarily isolated in the form of their mono- or di-salt, the salt-forming acids preferably being selected from hydrochloric acid, hydrobromic acid and oxalic acid.

The compounds of the present invention have been found to have neuroprotectant and/or potential antidepressant activity.

The present invention also includes use of established animal models for testing for neuroprotectant and/or potential antidepressant activity of N-propargyphentermine or derivatives having the following general formula:

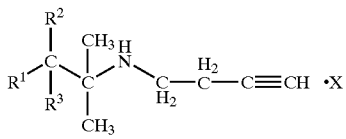

where

R$^1$ and/or R$^2$ and/or R$^3$ one or more phenyl, pyridinyl, pyrryl, furanyl, quinoline, isoquinoline, indolyl, naphthyl, thienyl or similar aryalkyl (where arylalkyl is defined as an aromatic structure such as a phenyl, pyridinyl, pyrryl, furanyl, quinoline, isoquinoline, indolyl, naphthyl, thienyl or similar aryl group combined with linear or branched or cyclic alkyl chain consisting of between 1 and 10 carbons), substituted arylalkyl, (where substituted arylalkyl is defined as an aromatic structure such as a phenyl, pyridinyl, pyrryl, furanyl, quinoline, isoquinoline, indolyl, naphthyl, thienyhl or similar aryl group combined with a linear or branched or cyclic alkyl chain consisting of between 1 and 10 carbons and substituted with one or more groups consisting of Cl, F, Br, OH, CF$_3$, NH$_3$, NO$_2$, alkoxy, alkylthiol, thiol or similar C$_1$–C$_8$ alkyl, substituted alkyl, alkenyl, alkynyl groups, X when present is a salt-forming acid, The compound can be administered in sufficient amounts to bestow neuroprotectant and/or antidepressant activity.

Synthesis of N-propargyphentermine

The N-propargylphentermine compounds of the present invention have been prepared as set forth below. N-propargyl derivatives of phentermine which possesses the characteristics of formula (I) can also be synthesized. The structure of phentermine is provided below. N-propargylphentermine can also be evaluated for monoamine oxidase-A- and monoamine oxidase-B-inhibiting properties, neuroprotective activity and for properties indicative of inhibition of amine uptake.

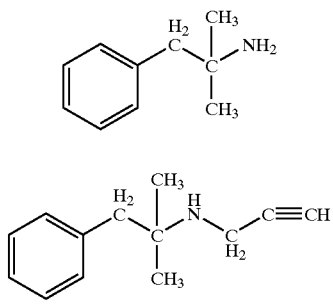

Phentermine

N-Propargylphentermine (I) can be prepared directly from phentermine by reaction with propargyl bromide. Phentermine is reacted with a molar equivalent of propargyl bromide in acetonitrile with excess potassium carbonate at room temperature for 24 hours. A mixture of products (N-substituted and N,N-distributed) is obtained, although this reaction favors the production of N-propargylphentermine. The resulting material is then filtered and dried, and chromatography on silica gel is used to purify the desired product.

The following typical compounds (CVT-PP019 and CVT-PP022) selected from the CVT-PP series were prepared as described above as examples.

CODE# CVT-PP019

Chemical Name: N-propargylphentermine

Formula: $C_{13}H_{17}N$

Molecular Weight: 187

Structure:

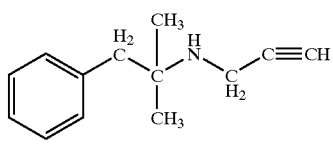

CODE # CVT-PP022

Chemical Name: p-chloro-N-propargylphentermine

Formula: $C_{13}H_{16}NCl$

Molecular Weight: 221.5

Structure:

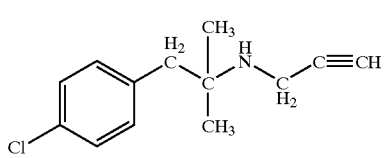

Biological Activity of Typical Compounds

The typical compounds PP019 and PP022 were tested in biochemical assays and in animals as follows.

The activity of the compound was initially determined in vitro at doses of $1 \times 10^{-4}$ and $1 \times 10^{-5}$ M for its ability to inhibit monoamine oxidase-A and monoamine oxidase-B. If the substance was active at these doses, a dose response relation was constructed and the effective dose ($ED_{50}$) determined. Each compound was also tested ex vivo for monoamine oxidase-inhibiting activity; ex vivo for serotonin-, dopamine- and noradrenaline-elevating activity; ex vivo for 5-hydroxyindoleacetic acid-reducing activity; ex vivo for protection against SDP-4-induced depletion of noradrenaline and in vitro for noradrenaline or serotonin uptake-inhibiting activity. If toxicity was encountered with the initial dose, the dose was reduced until one was reached which was tolerated by the animals being tested.

Compounds of the general formula I have been found to possess at least one of monoamine oxidase-inhibiting, amine-elevating, 5-hydroxytryptamine uptake-inhibiting and neuroprotectant activity in animals.

EXAMPLE 1

Monoamine Oxidase-A-Inhibiting Activity In Vitro

The compounds were evaluated for in vitro monoamine oxidase-A-inhibiting activity using the radiochemical procedure of Lyles and Callingham (1982) employing radiolabeled 5-hydroxytryptamine as substrate for monoamine oxidase-A. Various concentrations of the compounds of interest were incubated in appropriately diluted homogenates of rat brain or liver in a 0.2 M potassium phosphate buffer. Incubations proceeded at 37° C. for 10 minutes. Incubation was terminated by the addition of acid and the radiolabeled product (5-hydroxyindoleacetic acid) was extracted and quantified by liquid scintillation counting procedures. Incubations were done in triplicate and incubations from animals injected with (−)-deprenyl were included for comparison. The percent inhibition of monoamine oxidase-A activity compared to controls containing no drug was calculated. Results using rat brain and liver homogenates are summarized in Table 1.

Reference: Lyles, G. A. and Callingham, B. A. (1982). In vitro and in vivo inhibition by benserazide of clorgyline-resistant amine oxidases in rat oxidases in rat cardiovascular tissues. Biochem. Pharmacol. 31:1417–1424.

TABLE 1

$IC_{50}$ values for in vitro inhibition of rat brain monoamine oxidase-A by various concentrations of N-propargylphentermine (PP019), (−)-deprenyl and phenelzine

| CVT # | Tissue | $IC_{50}$ for inhibition of monoamine oxidase A |
|---|---|---|
| CVT-PP019 HCl | brain | $5.3 \times 10^{-5}$M |
| CVT-PP022 HCl | brain | $1.6 \times 10^{-4}$M |
| phenelzine.$H_2SO_4$ | brain | $1.3 \times 10^{-4}$M |
| (−) deprenyl HCl | brain | $2.8 \times 10^{-7}$M |

EXAMPLE 2

Monoamine Oxidase-A-Inhibiting Activity Ex Vivo

The compounds were evaluated for ex vivo monoamine oxidase-A inhibiting activity using the radiochemical procedure of Lyles and Callingham (1982) employing radiolabeled 5-hydroxytryptamine as substrate for monoamine oxidase-A. The compounds of interest were injected intraperitoneally using water as a vehicle. Animals were killed by decapitation and the brains and livers immediately removed and frozen until assay for monoamine oxidase-A activity. Tissues were homogenized and appropriately diluted in buffer prior to incubation. Incubations proceeded at 37° C. for 10 minutes. Incubation was terminated by the addition of acid and the radiolabeled product (5-hydroxyindoleacetic acid) was extracted and quantified by liquid scintillation counting procedures. Incubations were done in triplicate and incubations from animals injected with (−)-deprenyl were included for comparison. The percent inhibition of monoamine oxidase-A activity compared to controls containing no drug was calculated. Results using rat brain and liver homogenates are summarized in Table 2. Reference: Lyles, G. A. and Callingham, B. A. (1982). In vitro and in vivo inhibition by benserazide of clorgyline-resistant amine oxidases in rat cardiovascular tissues. Biochem. Pharmacol. 31:1417–1424.

TABLE 3

$IC_{50}$ values for in vitro inhibition of rat brain monoamine oxidase-B by various concentrations of N-proparglyphentermine (PP019), (−)-deprenyl and phenelzine.

| CVT # | Tissue | $IC_{50}$ for inhibition of monoamine oxidase B |
|---|---|---|
| CVT-PP019 HCl | brain | $5.7 \times 10^{-6}$M |
| CVT-PP022 HCl | brain | $4.0 \times 10^{-6}$M |
| phenelzine.$H_2SO_4$ | brain | $2.6 \times 10^{-5}$M |
| (−) deprenyl HCl | brain | $2.2 \times 10^{-9}$M |

TABLE 2

Ex vivo inhibition of rat brain and liver monoamine oxidase-A by combined treatment of DSP4 (50 mg/kg) with N-propargylphentermine (CVT-PP019) (10 mg/kg) or (−)-deprenyl (10 mg/kg).

| Compound | Period following injection | n | Route | Tissue | % Inhibition Monoamine Oxidase-A |
|---|---|---|---|---|---|
| Control/Control | 7 days | 5 | i.p. | brain | 1.1 ± 3.5 |
| CVT-PP019/DSP4 | 7 days | 5 | i.p. | brain | −16.4 ± 4.9 |
| CVT-PP022/DSP4 | 7 days | 5 | i.p. | brain | 2.5 ± 5.2 |
| Deprenyl/DSP4 | 7 days | 5 | i.p. | brain | −14.2 ± 9.3 |
| Control/DSP4 | 7 days | 5 | i.p. | brain | −3.4 ± 7.6 |
| Control/Control | 7 days | 5 | i.p. | liver | 2.0 ± 8.9 |
| CVT-PP019/DSP4 | 7 days | 5 | i.p. | liver | −20.1 ± 4.4 |
| CVT-PP022/DSP4 | 7 days | 5 | i.p. | liver | 5.9 ± 4.1 |
| Deprenyl/DSP4 | 7 days | 5 | i.p. | liver | 9.1 ± 6.0 |
| Control/DSP4 | 7 days | 5 | i.p. | liver | −7.3 ± 6.3 |

Controls received distilled water.
Values are the mean ± the standard error based on (n) determinations.
No significant inhibition of MAO-A is demonstrated 7 days after treatment.

EXAMPLE 3

Monoamine Oxidase-B-Inhibiting Activity In Vitro

The compounds were evaluated for in vitro monoamine oxidase-B inhibiting activity using the radiochemical procedure of Lyles and Callingham (1982) employing radiolabeled β-phenylethylamine as substrate for monoamine oxidase-B. Various concentrations of the compounds of interest were incubated in appropriately diluted homogenates of rat brain or liver in a 0.2 M potassium phosphate buffer. Incubations proceeded at 37° C. for 10 minutes. Incubation was terminated by the addition of hydrochloric acid and the radiolabeled product (phenylacetic acid) was extracted and quantified by liquid scintillation counting procedures. Incubations were done in triplicate and incubations containing pheneizine or (−)-deprenyl were included for comparison. The percent inhibition of monoamine oxidase-B activity compared to controls containing no drug was calculated. Results using rat brain and liver homogenates are summarized in Table 3. Reference: Lyles, G. A. and Callingham, B. A. (1982). In vitro and in vivo inhibition by benserazide of clorgyline-resistant amine exodiases in rat cardiovascular tissues. Biochem. Pharmacol, 31:1417–1424.

EXAMPLE 4

Monoamine Oxidase-B-Inhibiting Activity Ex Vivo

The compounds were evaluated for ex vivo monoamine oxidase-B-inhibiting activity using the radiochemical procedure of Lyles and Callingham (1982) employing radiolabeled β-phenylethylamine as substrate for monoamine oxidase-B. The compounds of interest were injected intraperitoneally in water. Animals were killed by decapitation and the brains and livers immediately removed and frozen until assay for monoamine oxidase-B activity. Tissues were homogenized and appropriately diluted in buffer prior to incubation. Incubations proceeded at 37° C. for 10 minutes. Incubation was terminated by the addition of acid and the radiolabeled product (phenylacetic acid) was extracted and quantified by liquid scintillation counting procedures. Incubations were done in triplicate and incubations from animals injected with (−)-deprenyl were included for comparison. The percent inhibition of monoamine oxidase-B activity compared to controls containing no drug was calculated. Results using rat brain and liver homogenates are summarized in Table 4. Reference: Lyles, G. A. and Callingham, B. A. (1982). In vitro and in vivo inhibition by benserazide of clorgyline-resistant amine oxidases in rat cardiovascular tissues. Biochaem. Pharmacol. 31:1417–1424.

TABLE 4

Ex vivo inhibition of rat brain and liver monoamine oxidase-B by combined treatment of DSP4 (50 mg/kg) with N-propargylphentermine (CVT-PP019) (109 mg/kg) or (−)-deprenyl (10 mg/kg).

| Compound | Period following injection | n | Route | Tissue | % Inhibition Monoamine Oxidase-B |
|---|---|---|---|---|---|
| Control/Control | 7 days | 5 | i.p. | brain | 2.1 ± 5.8 |
| CVT-PP019/DSP4 | 7 days | 5 | i.p. | brain | −9.4 ± 3.0 |
| CVT-PP022/DSP4 | 7 days | 5 | i.p. | brain | 17.5 ± 5.6 |
| Deprenyl/DSP4 | 7 days | 5 | i.p. | brain | 55.2 ± 2.6* |
| Control/DSP4 | 7 days | 5 | i.p. | brain | 1.1 ± 5.0 |
| Control/Control | 7 days | 5 | i.p. | liver | −0.8 ± 9.7 |
| CVT-PP019/DSP4 | 7 days | 5 | i.p. | liver | −10.1 ± 6.6 |
| CVT-PP022/DSP4 | 7 days | 5 | i.p. | liver | 12.6 ± 5.3 |
| Deprenyl/DSP4 | 7 days | 5 | i.p. | liver | 25.0 ± 2.3* |
| Control/DSP4 | 7 days | 5 | i.p. | liver | −8.5 ± 6.0 |

Controls received distilled water.
Values are the mean ± the standard error based on (n) determinations.
*Significant inhibition of MAO-B is demonstrated 7 days after treatment ($p < 0.05$).

EXAMPLE 5

Prevention of DSP-4 Neurotoxicity Ex Vivo

Neuroprotectant activity was evaluated by examining the prevention of DSP-4 induced noradrenaline depletion in mouse hippocampus as described previously (Yu et al., 1994). Briefly, mice were injected (i.p.) with either water or potential neuroprotectants (10 mg/kg in water). One hour later they were injected with either water or DSP-4 (50 mg/kg in water). One week later the mice were killed and the brains removed and the hippocampus dissected out. The hippocampus was frozen and saved for estimation of noradrenaline and other amine neurotransmitters and their metabolites (Sloley and Goldberg, 1991). The rest of the brain and the liver were frozen and retained for estimation of monoamine oxidase activities ex vivo as described earlier. Administration of CVT-PP019 or CVT-PP022 significantly protected against DSP-4-induced noradrenaline depletion (Tables 5 and 6). This neuroprotective effect was not significantly different from the neuroprotective effect demonstrated by deprenyl. Furthermore, CVT-PP019 and CVT-PP022 did not significantly affect either monoamine oxidase-A or monoamine oxidase-B activity in the brain or liver seven days after administration (refer to Tables 2 and 4). References: Yu, P. H., Davis, B. A., Fang, J. and Boulton, A. A. (1994), Neuroprotective effect of some monoamine oxidase-B inhibitors against DSP-4 induced noradrenaline depletion in the mouse hippocampus, J. Neurochem. 63:1820–1828. Sloley, B. D. and Goldberg J. I. (1991), Determination of y-glutamyl conjugates of monoamines by means of high-performance liquid chromatography with electrochemical detection and application to gastropod tissues, J. Chromatog. 567:49–56.

TABLE 5

Protection by CVT-PP019 against noradrenaline depletion in mouse hippocampus produced by DSP-4.

| First Treatment | Second Treatment | n | % NA Restoration |
|---|---|---|---|
| Water | Water | 5 | n/a |
| (−)-deprenyl 10 mg/kg | DSP-4 50 mg/kg | 5 | 97.2 |
| CVT-PP019 10 mg/kg | DSP-4 50 mg/kg | 5 | 114.6 |
| Water | DSP-4 50 mg/kg | 5 | n/a |

Values are the means ± the standard errors based on n determinations. n/a not applicable.
*Significantly different from vehicle, PP019 and deprenyl treated animals.

TABLE 6

Protection by CVT-PP022 against noradrenaline depletion in mouse hippocampus produced by DSP-4.

| First Treatment | Second Treatment | n | % NA Restoration |
|---|---|---|---|
| Water | Water | 5 | n/a |
| (−)-deprenyl 10 mg/kg | DSP-4 50 mg/kg | 5 | 90.3 |
| CVT-PP022 10 mg/kg | DSP-4 50 mg/kg | 5 | 70.5 |
| Water | DSP-4 50 mg/kg | 5 | n/a |

Values are the means ± the standard errors based on n determinations. n/a not applicable
*Significantly different from vehicle, PP022 and deprenyl treated animals.

EXAMPLE 6

Inhibition of noradrenaline and serotonin uptake in vitro

The ability of N-propargylphentermine and related derivatives to inhibit monoamine uptake was evaluated in vitro by examining the effects of said compounds on the uptake of radiolabeled noradrenaline and serotonin into fresh rat hippocampal and striatal prisms, respectively according to the method described in Martin et al., (1978). Animals were killed by decapitation and the hippocampus or striatum were removed and placed in ice cold incubation medium. Prisms were prepared using a tissue chopper, resuspended in 800 volumes of incubation medium containing 12.5 $\mu$M nialamide to inhibit amine metabolism and stored on ice until used. 0.8 ml of ice cold prism of suspension per test tube was used. Each test tube was pre-incubated for 5 minutes at 37° C. At this time each test tube was placed on ice and the appropriate drug solution or control was added. This was rapidly followed by the addition of the radiolabled amine (titrated noradrenaline or serotonin, 0.01 μM, specific activity about 13.5 Ci/mmol). The mixture was incubated for 10 minutes at 37° C. The incubations were then filtered and washed using a cell harvester and the radioactivity retained on the filters was measured using a scintillation counter. The percent inhibition of amine uptake compared to controls containing no drug was calculated. Reference: Maretin I. L., Baker G. B. and Mitchell, P. R. (1978). The effect of viloxaine hydrochloride on the transport of noradenaline, dopamine, 5-hydroxytryptamine and gamma-amino-butyric acid in rat brain tissue. Neuropharmacology 17:421–423.

TABLE 7

Effect of Desipramine, Fluoxetine, CVT-PP019 and CVTA-PP022 on noradrenaline (NA) and serotonin (5-HT) uptake into rat hippocampal and striatal prisms, respectively.

| Compound (1 × 10$^2$M) | % inhibition NA uptake | % inhibition 5-HT uptake |
|---|---|---|
| Desipramine | 99 ± 3 | N.D. |
| Fluoxetine | N.D. | 99 ± 1 |
| CVT-PP019 | 77 ± 3 | 68 ± 2 |
| CVT-PP022 | 93 ± 2 | 89 ± 1 |

Values are the mean ± the standard error based on a sample size of 4.
N.D. not done.

Reasonable modifications of the inventions disclosed herein are well within the scope of those skilled in the art, and are also intended to be within the scope of the present invention. The scope of the invention is not intended to be limited by the specific examples set out herein. All of the references set forth in this application are herein incorporated by reference in their entirety.

We claim:

1. An N-propargylphentermine compound having the following formula:

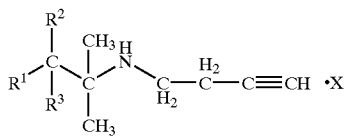

where
  $R^1$ and/or $R^2$ and/or $R^3$ are independently one or more phenyl, pyridinyl, pyrryl, furanyl, quinolinyl, isoquinolinyl, indolyl, naphthyl, thienyl, arylalkyl, substituted arylalkyl, $CH_3$, Cl, F, Br, OH, $CF_3$, $NH_2$, $NO_2$, alkoxy, alkylthiol, thiol, $C_1$–C8 alkyl, substituted alkyl, alkenyl, or alkynyl groups, and
  X when present is a salt-forming acid.

2. A pharmaceutical composition comprising the N-propargylphentermine compound according to claim 1 in combination with a pharmaceutically acceptable carrier.

3. A method for providing neuroprotection in a patient in need thereof, comprising administering to the patient a neuroprotective effective amount of an N-propargylphentermine compound according to claim 1.

4. A method of treating depression in a patient in need thereof, comprising administering to the patient an anti-depressant effective amount of an N-propargylphentermine compound according to claim 1.

5. A method of providing neuroprotection and treating depression in a patient in need thereof, comprising administering to the patient a neuroprotective and anti-depressant effective amount of an N-propargylphentermine compound according to claim 1.

6. A method of treating neurodegenerative disease in a patient in need thereof, comprising administering to the patient an anti-neurodegenerative effective amount of N-propargylprmine compound according to claim 1.

7. The method according to claim 3, 4, 5 or 6 wherein said N-propargylphentermine compound is administered orally, transdermally or as an injection.

8. A pharmaceutical composition suitable for providing protection against depression comprising an anti-depressant effective amount of the N-propargylphentermine compound according to claim 7 in combination with a pharmaceutically acceptable carrier.

9. A pharmaceutical composition suitable for providing neuroprotection comprising a neuroprotective effective amount of the N-propargylphentermine compound according to claim 7 in combination with a pharmaceutically acceptable carrier.

10. A pharmaceutical composition suitable for providing neuroprotection and protection against depression comprising an anti-depressant and neuroprotective effective amount of N-propargylphentermine compound according to claim 7 in combination with a pharmaceutically acceptable carrier.

11. A pharmaceutical composition suitable for treating a neurodegenerative disease comprising an anti-neurodegenerative effective amount of the N-propargylphentermine compound according to claim 7 in combination with a pharmaceutically acceptable carrier.

12. A method for providing neuroprotection in a patient in need thereof comprising administering to the patient a neuroprotective effective amount of an N-propargylphentermine compound according to claim 7.

13. A method of treating depression in a patient in need thereof comprising administering to the patient an anti-depressant effective amount of an N-propargylphentermine compound according to claim 7.

14. A method of providing neuroprotection and treating depression in a patient in need thereof comprising administering to the patient a neuroprotective and anti-depressant effective amount of an N-propargylphentermine compound according to claim 7.

15. A method of treating a neurodegenerative disease in a patient in need thereof, comprising administering an anti-neurodegenerative effective amount of N-propargylphentermine compound according to claim 7.

16. The method according to any one of claims 12–15, wherein the N-propargylphentermine compound is administered orally, transdermally or as an injection.

* * * * *